US010433796B2

(12) United States Patent
Bystrov et al.

(10) Patent No.: US 10,433,796 B2
(45) Date of Patent: Oct. 8, 2019

(54) SELECTING TRANSFER FUNCTIONS FOR DISPLAYING MEDICAL IMAGES

(71) Applicant: KONINKLIJKE PHILIPS N.V., Eindhoven (NL)

(72) Inventors: Daniel Bystrov, Hamburg (DE); Astrid Ruth Franz, Hamburg (DE); Nicole Schadewaldt, Norderstedt (DE); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/572,169

(22) PCT Filed: Jun. 17, 2016

(86) PCT No.: PCT/EP2016/063994
§ 371 (c)(1),
(2) Date: Nov. 7, 2017

(87) PCT Pub. No.: WO2016/202973
PCT Pub. Date: Dec. 22, 2016

(65) Prior Publication Data
US 2018/0122057 A1    May 3, 2018

(30) Foreign Application Priority Data

Jun. 19, 2015 (EP) .................... 15172951

(51) Int. Cl.
*G06T 19/00* (2011.01)
*A61B 6/03* (2006.01)
(Continued)

(52) U.S. Cl.
CPC .............. *A61B 6/032* (2013.01); *A61B 5/055* (2013.01); *A61B 5/743* (2013.01); *A61B 8/463* (2013.01);
(Continued)

(58) Field of Classification Search
None
See application file for complete search history.

(56) References Cited

U.S. PATENT DOCUMENTS 9,600,879 B2    3/2017  Bystrov
2010/0014729 A1  1/2010  Choi
(Continued)

OTHER PUBLICATIONS

Pekar, et al., "Fast detection of meaningful isosurfaces for volume data visualization" Visualization, 2001.
(Continued)

*Primary Examiner* — Yanna Wu (57) ABSTRACT

System and related method to visualize image data. The system comprises an input port (IN) for receiving i) image data comprising a range of intensity values converted from signals acquired by an imaging apparatus in respect of an imaged object, and ii) a definition of a first transfer function configured to map a data interval within said range of said intensity values to an image interval of image values. A transition region identifier (TRI) identifies from among intensity values outside said data interval, one or more transition intensity values representative of a transition in composition and/or configuration of said object or of a transition in respect of a physical property in relation to said object. A transfer function generator (TFG) generates for said intensity values outside said data interval a second transfer function. The second transfer function is non-linear and has a respective gradient that is locally maximal around said transition intensity values. A renderer (RD) then renders, on a display unit (MT), a visualization of at least a part of said image data based on the two transfer functions.

13 Claims, 5 Drawing Sheets

(51) Int. Cl.
*G06T 5/00* (2006.01)
*A61B 5/055* (2006.01)
*A61B 5/00* (2006.01)
*A61B 8/00* (2006.01)

(52) U.S. Cl.
CPC .............. *G06T 5/007* (2013.01); *G06T 19/00* (2013.01); *G06T 2207/10024* (2013.01); *G06T 2207/10072* (2013.01); *G06T 2207/20208* (2013.01); *G06T 2207/30004* (2013.01); *G06T 2210/41* (2013.01)

(56) References Cited

U.S. PATENT DOCUMENTS

2011/0228997 A1   9/2011   Sharp
2015/0022523 A1*  1/2015   Murray .................. G06T 15/08
                                                          345/426

OTHER PUBLICATIONS

Cheng, et al., "Real-time adjustment of transfer function for Fourier volume rendering", Journal of Electronic Imaging, Oct. 26, 2011.
Kniss, et al., "Gaussian transfer functions for multi-field volume visualization", VIS 2003.
Kindlmann, et al., "Semi-automzatic generation of transfer functions for direct volume rendering", Volume Visualization, 1998.

* cited by examiner

SELECTING TRANSFER FUNCTIONS FOR DISPLAYING MEDICAL IMAGES

CROSS REFERENCE TO RELATED APPLICATIONS

This application is the U.S. National Phase application under 35 U.S.C. § 371 of International Application No. PCT/EP2016/063994, filed Jun. 17, 2016, published as WO 2016/202973 on Dec. 22, 2016, which claims the benefit of European Patent Application Number 15172951.4 filed Jun. 19, 2015. These applications are hereby incorporated by reference herein.

FIELD OF THE INVENTION

The invention relates to an image processing system, an image processing method, a computer program element, and a computer readable medium.

BACKGROUND OF THE INVENTION

In the visualization of medical images it is a clinical standard procedure to select a certain "level" and "window" setting when, for instance, a tomographic medical image is to be viewed. This procedure is sometimes called the level-window technique. The aim is to enhance the contrast in a certain intensity range characteristic for a certain anatomical region and to use the gamut from, say, black to white to show the selected range. Since CT images have a well-defined scale (in Hounsfield units (HU)) it is very common to select a certain gray value window for a specific reviewing task, e.g. a dedicated lung window or bone window is defined. For other imaging modalities, such as MRI (magnetic resonance imaging), choosing the right visualization is more complicated since the scale is not as quantitative as in CT imaging. Therefore, MR images are very often normalized and gradient bias fields are suppressed, which is a technique necessary to allow window level settings to be useful beyond small, localized regions. Even without this, a similar level and window mapping as in CT is then used to (re)view MR datasets.

It has been observed by the Applicant that despite there being an abundance of predefined level-window settings dedicated to different anatomical contexts and tasks, some anatomical information may still slip the attention of the clinician during image (re)viewing.

SUMMARY OF THE INVENTION

There may therefore be a need for an alternative system or method to visualize image data.

The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system, comprising:

an input port for receiving i) image data comprising a range of intensity values converted from signals acquired by an imaging apparatus in respect of an imaged object, and ii) a definition of a first transfer function configured to map a data interval within said range of said intensity values to an image interval of image values;

a transition region identifier configured to identify from among intensity values outside said data interval, referred to herein as outside intensity values, one or more transition intensity values (also referred to herein as transition points) representative of a transition in composition and/or configuration of said object or of a transition in respect of a physical property in relation to said object;

a transfer function generator configured to generate for said outside intensity values, at least one second transfer function, said at least one second transfer function being non-linear and having a respective non-zero gradient (slope) at or around the one or more transition intensity values.

a renderer configured to render, on a display unit, a visualization of at least a part of said image data based on the at least two transfer functions.

In other words, the slope of the second transfer function is at least locally maximal at or around the transition points. That is, there are respective neighborhoods around the one or more transition points (said respective neighborhoods including the respective transition point), and in each neighborhood there is at least one outside intensity value that has non-zero gradient or even a gradient that is a locally maximal for the respective neighborhood.

This allows enhanced contrast at these transition points thus providing to a user structural clues encoded by the outside range intensity values. Information content of the visualization is increased and yet an "information overload" is prevented because the enhanced contrast is restricted to where it matters, namely, where transition is represented.

According to one embodiment, the transition region identifier is configured to compute at least one iso-surface for at least one of the outside intensity values, wherein the identification of said one or more transition intensity values is based on an evaluation operation by the transition region identifier (TRI) of said one or more iso-surfaces.

According to one embodiment, said evaluation operation includes computing a metric, said metric being any one or more of the following: a surface area of said at least one iso-surface and/or a gradient across said iso-surface and/or computing an integral of the gradient or an absolute or signed value of the gradient.

According to one embodiment, the transition intensity value is identified if said metric is above or below a threshold or if said metric assumes at least a local extremum.

According to one embodiment, the renderer is configured to include in the visualization one or more contour-lines of the one or more iso-surfaces.

According to one embodiment, the image data is any of: a 2D X-ray image, a 3D computed tomography image volume, a magnetic resonance image data, a 2D or 3D ultrasound image.

According to one embodiment, the composition transition includes material (e.g. tissue) type transition or a transition between material type and background.

The proposed system usefully supplements standard viewing of medical images (eg, tomographic images or other). As mentioned in the background above, this standard viewing is performed using a task dependent transfer function (the first transfer function) for a primary region of interest. The first transfer function is defined by a specific gray value level and "window" around said level. Previously, outside this window the displayed visualization is "bleeding out" and thus anatomical information is hidden. To remedy this, the proposed system constructs an additional (the second) (color) transfer function outside the selected window so that color changes are chosen at optimal, anatomically meaningful positions. Contrast is selectively enhanced by the second transfer function only around the identified transition intensity values (also referred to herein as transition points). In other words, color changes and contrast variations outside the gray value window can be chosen optimally to better visualize only those points/ regions in the outside range that represent transitions. Optionally a dataset could also be displayed outside the gray level window using iso-lines at these meaningful transitions.

The terms "first" and "second" transfer function(s) should be construed broadly.

Initially, the first transfer function is defined on the inside range and outside range. The second transfer function is then computed for the outside range only and can then be thought of as extending into the inside range (of the first transfer function) where it is identical to the first transfer function. However, mathematically, the two transfer functions may also be looked at as sections of a single transfer function, each section defined only on the inside and outside range respectively, the single transfer function being then defined on a domain formed by the (set-theoretic) union of the inside and outside range. Also, the terms "first" and "second" are names used to distinguish the two function (-sections) and are not to be construed so as to necessarily impart a sense of "priority" of one over to the other. Still, in some use scenarios (but not necessarily in all scenarios) the first transfer function will be associated with the primary region of interest which the clinician is primarily concerned with when defining or selecting the (initial) level-window stetting, that is, when defining the first transfer function.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
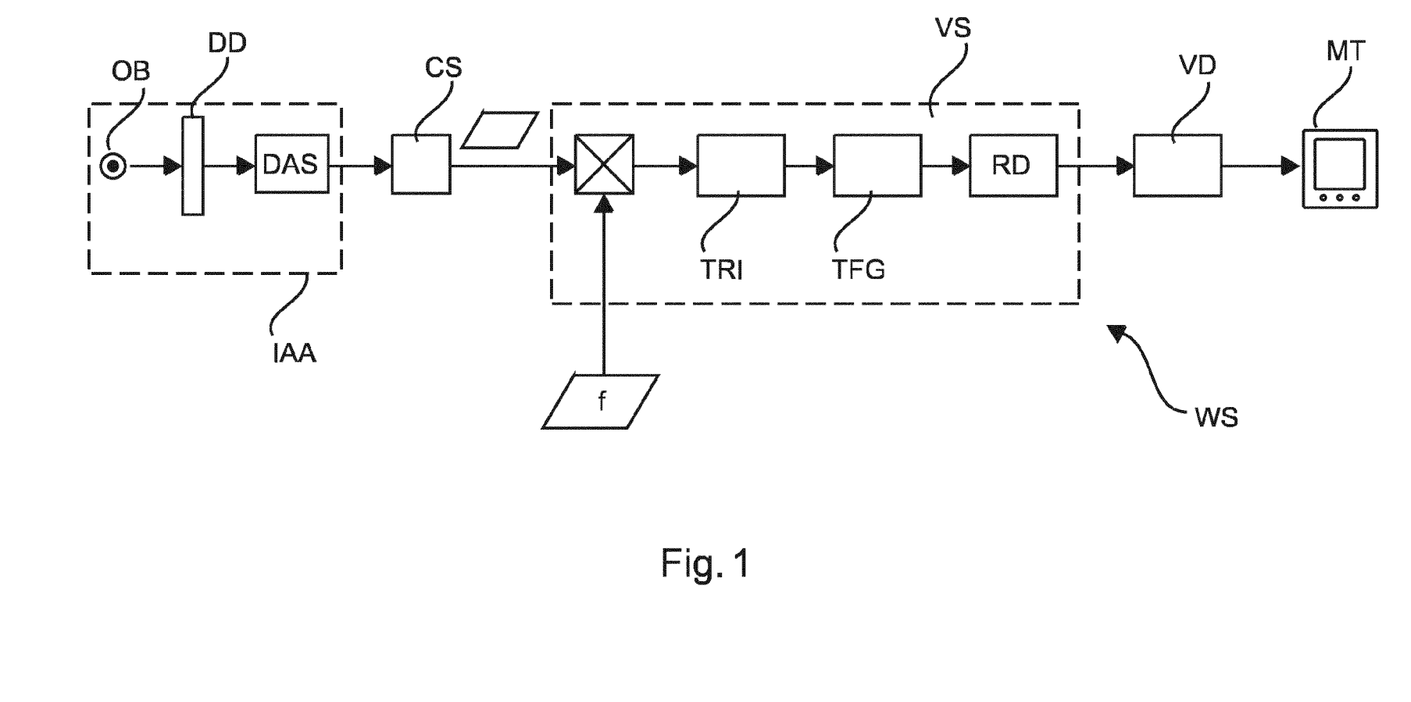
FIG. 1 shows an imaging system.

With reference to FIG. 1 there is shown an imaging system comprising an image acquisition apparatus IAA and an image processing (sub-)system VS or a "visualizer". The visualizer can be implemented as a software routine in a (medical image) viewing platform executed on a general purposed computing unit or on a dedicated workstation WS. Image raw data supplied by the image acquisition apparatus IAA can be processed in a manner to be described in more detail below to produce images viewable on a display device MT such as a computer monitor or the display screen of a portable communication device (smartphone, tablet, etc). The image data as supplied by the image acquisition apparatus IAA can be transferred in a wired or wireless network or by any other means (e.g. by USB dongle, etc) to the visualizer VS. The visualizer VS may be also implemented as a (dedicated) FPGA (A field-programmable gate array) or as hardwired chip. The visualizer may be integrated into a dedicated graphics chip or graphics processor of the computing unit or work station WS.

The image data as supplied by the image acquisition apparatus IAA can be 2D 3D. Examples of the image acquisition apparatus IAA envisaged herein are a 2D radi- ography system such as a C-arm system, a computed tomography scanner (CT), a magnetic resonance imager MRI or any other imaging modality such as an ultrasound imaging system, etc.

The image acquisition apparatus is particularly envisaged for medical applications although other fields of applications are not excluded herein. The image acquisition apparatus IAA is particular configured to acquire image signals about the internals of an object OB of interest although processing of image signals representative of the outside of the object OB of interest is not excluded herein. For brevity, the term "object of interest" OB as used herein includes animate or inanimate objects. In particular the object is a human or animal patient or a part thereof, such as particular anatomy (thorax, abdomen, extremities, etc).

In general, the image acquisition apparatus IAA is capable of producing an interrogating signal to interrogate for the internal structure of the object. Examples of such an interrogating signal are x-ray radiation or other electro-magnetic radiation or non-electromagnetic signals such as ultrasound etc. The interrogating signal interacts with the object to modulate a response signal which is detected with a detection device DD. For instance, in the radiography embodiment, the detection device DD is an x-ray sensitive detector. In MRI the detection device DD comprises coils to pick-up electromagnetic pulses. In ultrasound, the detector device is a transducer configured to pick up ultrasound reflections, etc. That is, depending on the imaging modality used, the detection device is suitably configured to pick up the respective type of response signal.

The detected signals (intensity values) are then processed into digital form by a data acquisition unit DAS. The digitalized intensity data is then processed by conversion circuitry CS to convert the intensity data into a suitable numerical format, such as a range of Hounsfield units (CT numbers) used in CT. Hounsfield units (HU) are used to represent the radiological density of matter. Conventionally air has a radiological density of −1000 HU, water has a radiological density of 0 HU and that for bone may lie in the range 700 to around 3000 HU. The so converted intensity values are then forwarded as raw image data to visualizer VS to produce color signals at its output OUT which can be used to drive video circuitry VD of the imaging system which in turn controls the monitor MT to produce a display, that is, a visualization, of the (possibly format-converted) intensity values. "Color values" are used herein in a general, computer graphics sense, so includes in particular black, white and grey values and "color value" is not meant to be restricted to color imaging in the narrow sense such as RGB (red-green-blue) coding, etc. It will be understood that the intensities may be passed through further signal processing stages before being processed by the visualizer. For instance, in the CT embodiment, before conversion into the HU format, the intensity values are processed by a reconstruction module (not shown) that implements a suitable reconstruction algorithm (e.g. (filtered)-backward-projection (F)BP, statistical, algebraic or other iterative reconstruction techniques, etc.). The reconstruction operates on the acquired intensities (which are projections through the object along manifold directions) to reconstruct for a 3D set of intensity values and it is this 3D block of intensities that is then converted into HU format and forwarded for processing by the visualizer VS.

The intensity values as acquired by the image acquisition apparatus IAA encode information about the internal structure, e.g., configuration or composition of the object OB to be imaged. Depending on the interrogating signals used, the internal structure or composition of the object modulates a certain pattern onto the response signal. This pattern or modulation is maintained after conversion into suitable number range and is encoded in the image data as a tell-tale, spatial variation across the digital image data. More particularly the image data is organized into image elements (pixels or voxels) for instance, each image element being associated with a number such as Hounsfield unit in the CT embodiment. Variations of these numbers across those image elements can be thought then to represent certain structures of interest. Of particular interest in the image data are those sub sets of image elements that represent transitions of configuration or composition in the imaged object. For instance transitions from one material (in particular tissue) type to another (from fat to water for instance) or between background and tissue bone or any other types of transitions of interest. In some embodiments, the correspondence between the transitions and the way the image data encodes these variations may not always be direct and straightforward as it is X-ray imaging. In MRI for instance, the recorded measurements may not directly relate to said transitions.

The intensity values before or after conversion into the suitable numerical format (e.g., CT numbers) may be referred to herein as "raw image data" as this data as such is not normally suitable for visualizations (also, in the following we will no longer distinguish between intensity values and their numerical conversions/reconstructions, both being referred to herein as "intensity values" or simply "intensities").

Figure 2:
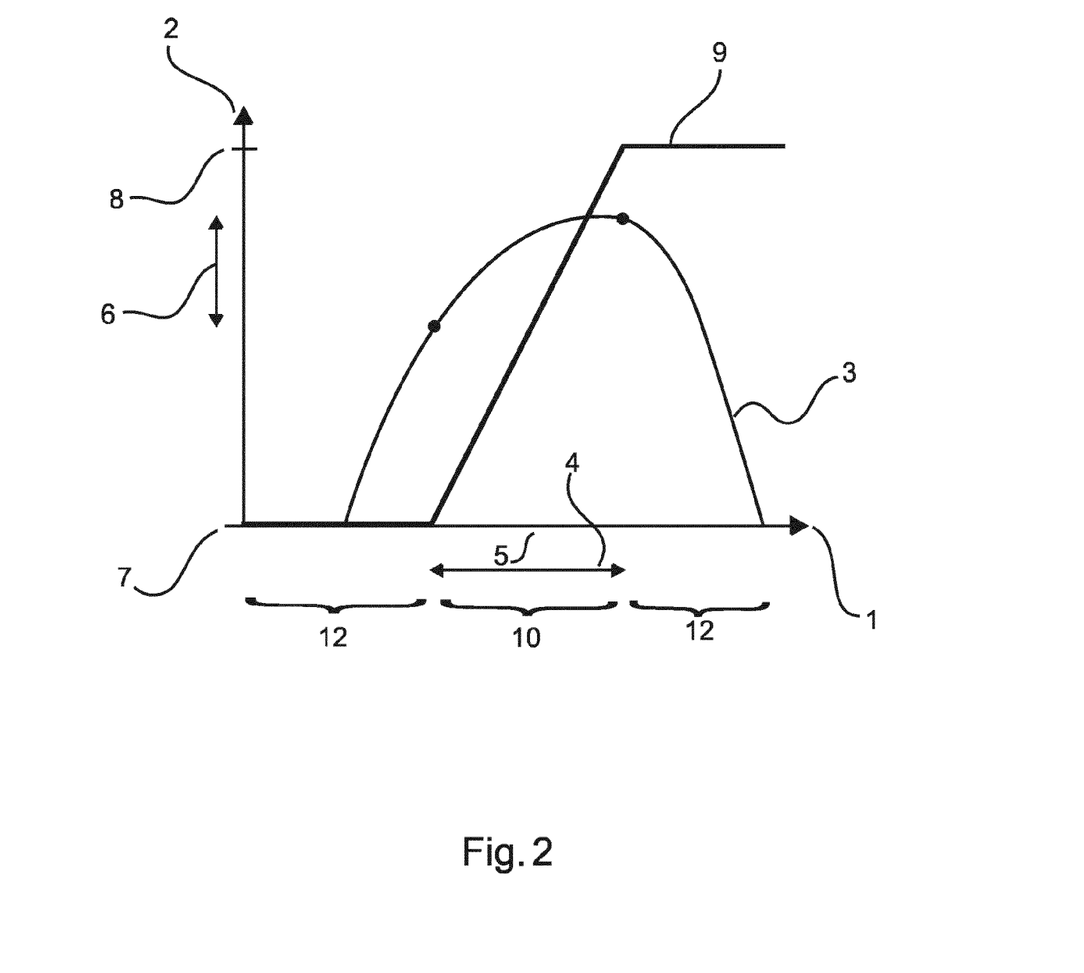
FIG. 2 shows a transfer function.

To prepare the raw data for visualization, a transfer function is used. A transfer function is configured to map the intensity values into suitable range of color values which can then be used to control operation of the actual visualization of the image data on screen MT. However, the image range, that is, the dynamics, of all intensity values can be quite large and differences between the same can be quite subtle. Therefore, mapping the entire range of intensity values to a (limited) range of image/color values may produce visualization where those possibly minute changes may simply not be discriminable. To get a hand on this problem, "viewing guidelines" have been published to inform the user which range of image data corresponds to certain objects of interest. Based on this information, the user can use the so called level-window technique to select a suitable range of image values ("window") centered around a particular image value of interest ("level") as shown in the illustration of FIG. 2 which also showing particulars of an image transfer function. A plurality of data/intensity values 1 are mapped to a plurality of image/color values 2. The intensity values 1 may for example represent Hounsfield units in a CT image and the image values 2 may for example represent color values such as grayscale values. In the level and window mapping technique, the distribution of pixel data values in an image are represented by pixel data value histogram 3, within which a user is interested in a particular window 4 centered about a data value level 5. The window may have particular physiological interest and give rise to a range of grayscale values 6 which may be less than the full scale of available image values between black 7 and white 8. In order to improve the grayscale contrast between data values within the window 4, the lowest data value in the window is conventionally mapped to black 7 and the highest data value mapped to white 8 using a linear mapping function 9. Data values at and below the lowest data value in the window are consequently mapped to black and those at and above the highest data value are mapped to white.

As can be seen in FIG. 2, traditionally, the selection of a certain window defines a partition on the range of intensity values as encoded in the received image. There is an inside range 10 and an outside range 12 of intensity values. The inside range of intensity values represent those values which are selected by the user and which are particularly suitable to visualize a particular anatomy or region of interest. Intensity values of the received image not within said image value that is intensity values outside said inside range are called correspondingly outside range intensity values, or outside intensity values for short. As can be seen in previous approaches the outside intensity values have been mapped altogether on constant values for instance, black or white. Thus, no information on structural transitions on the anatomy outside the region of interest can be provided.

Said differently, the currently used window-level technique imposes contextual "blinkers" on the human observer. In order to learn about another anatomy not represented by the selected window, the user is forced to select a different window/level to be able to view the structure of a different region of interest. The proposed visualizer VS offers a remedy for this situation. It still allows the user to choose, as before, an image transfer function tailored to the particular needs of the region of interest but unlike previous approaches outside structures are not completely whitewashed or equalized. In this manner the imagery produced by the proposed visualizer has a dual function. It first provides detailed structural information about the primary region of interest but still provides sufficient (in a manner to be explained in more detail below) structural image information on the secondary region of interest represented by intensity values from the outside range. The image information in respect of the outside intensity values is "sufficient" in the sense that at least certain transitions are still discernable by the user. In other words, the user is provided concurrently with anatomical context information outside the primary region.

Figure 3:
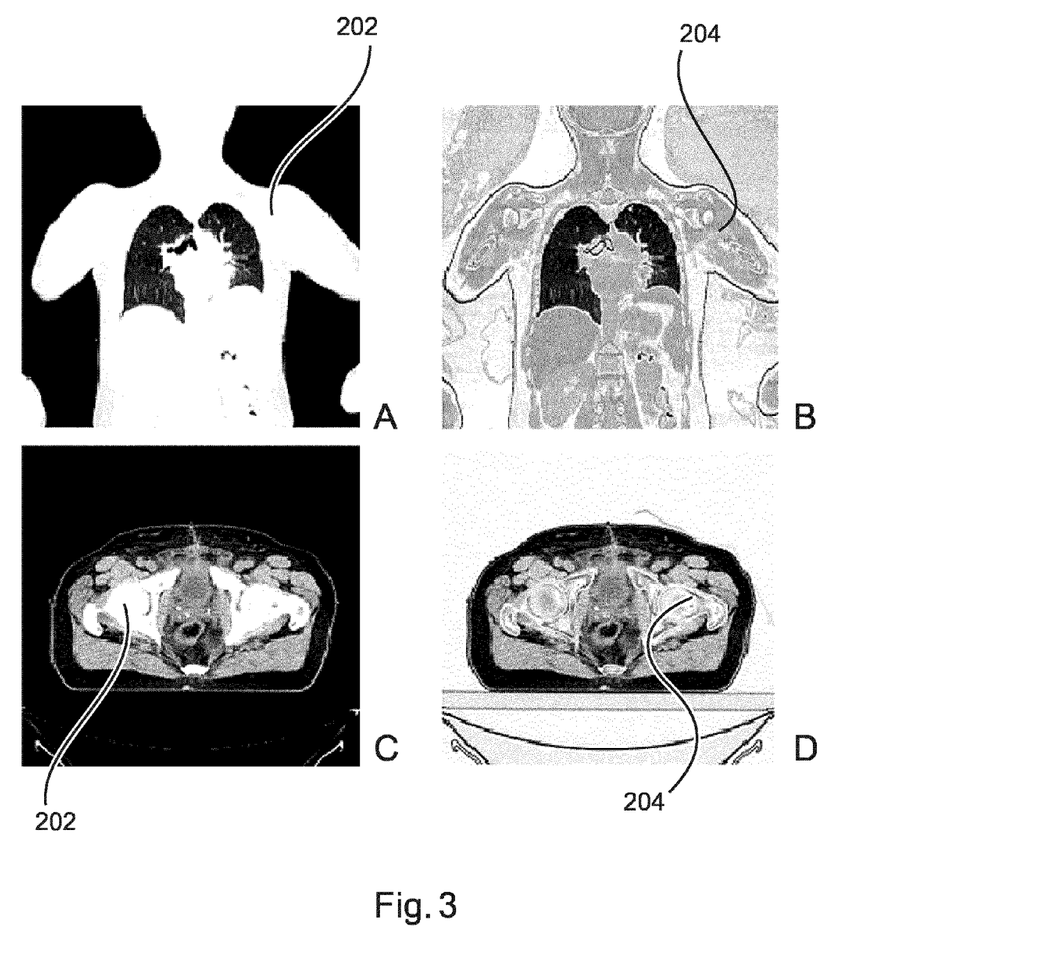
FIG. 3 shows conventional imagery compared to exemplary imagery obtainable by the imaging system as per FIG. 1.

FIG. 3 is an illustration of the traditional window technique versus the proposed visualizer VS. Outside range 12 is mapped to non-constant values by using a different, additional transfer function only for the outside range 12 whilst the inside range 10 is still rendered with the first transfer function. That is, outside range values are no longer mapped (as was previously done) to constant color values (such as black or white in a grey scale rendering) but the outside range 12 is are now "resolved" into more detail to lay bare transition structures by operation of the second (non-constant) transfer function supported on said outside range 12. The whole visualization is thus a combined rendering from (at least) two transfer functions.

Figure 5:
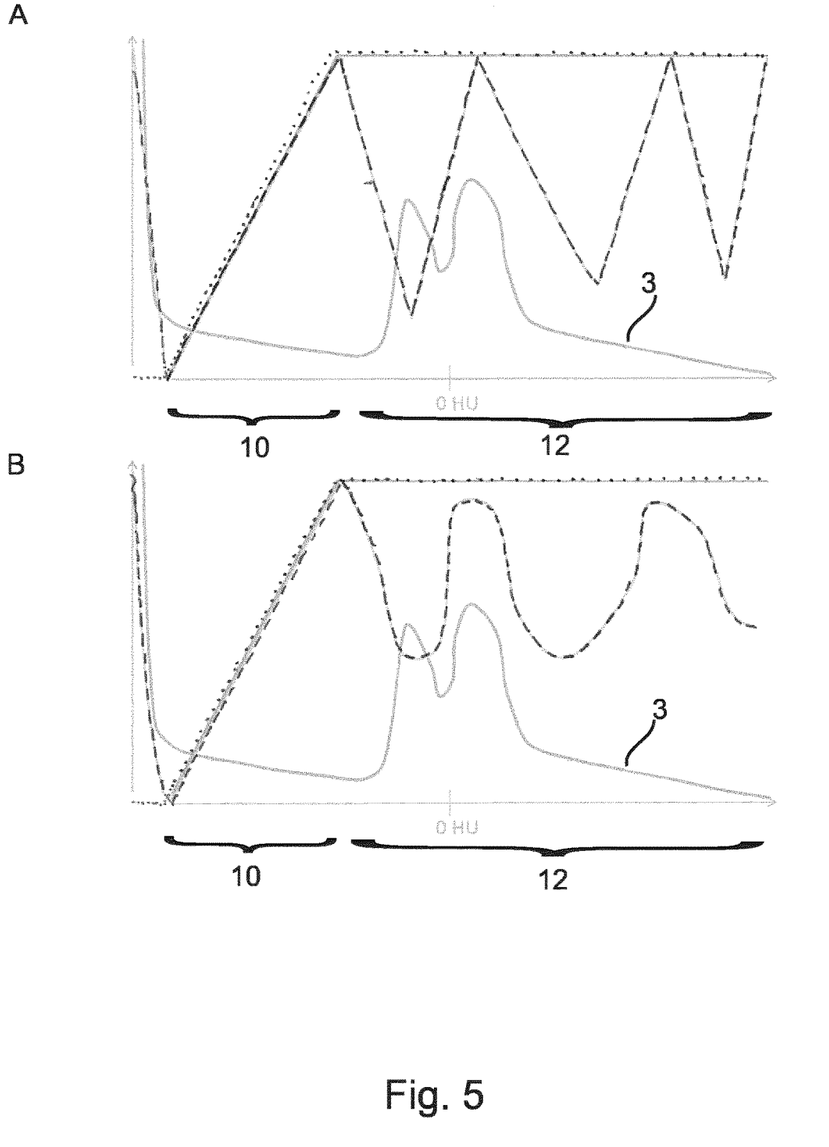
FIG. 5 shows further transfer functions.

FIG. 5 A,B shows in more detail two exemplary illustrations for the second transfer function (shown in dashed lines) as proposed herein, defined with a non-constant (non-zero gradient) part for the outside range 12. The second transfer function is shown superimposed on the first transfer function (shown in dotted lines) and histogram 3. Broadly, the second transfer function envisaged herein is in particular non-linear, e.g. oscillating (or otherwise) in the outside range 12 whilst the first transfer function is linear in the inside range 10.

The second transfer function for the outside range as per FIG. 5A is only piece-wise linear but non-linear over the whole of the outside range. The peaks of histogram, 3 are for air (very left) and fat/water (center). The first transfer function is constant in the outside range, so air gets mapped to black values and water, fat and bones to white values. The situation is completely different for the second transfer function which is non-constant on the outside range 12. The second transfer function reveals details of the outside range. In particular, fat (peak of dashed line) is rendered much darker than water (trough of dashed line) hence clearly showing the transition with the corresponding transition point marked up at "0 HU" on the x-axis. The second transfer function as per A is an example for lung imaging but this is exemplary only and in no way limiting.

The second transfer function for the outside range as per B is another example for a non-constant transfer function that is not linear in the outside range. In particular, this function is oscillating (but, as shown, not necessarily periodic). At fat and water peaks, the assigned grey values are nearly the same, but the part of the outside range in between the two is now mapped by a part of the second transfer function that has a strong gradient to clearly render the fat-water transition at 0 HU (=CT intensity 1000).

In both examples A,B, the first transfer function is maintained for the inside region so there is no "signal loss" and re-learning required for the clinician as the inside region will be rendered as before. It is only the outside region which is now resolved into details about transitions thanks to the operation of the newly proposed second transfer function.

Also, second transfer function may or may not use the entire grey value spectrum so it may or may not map to black or white inclusive, depending on the imaging application at hand. Having the second transfer function being non-linear in the outside range and having the first transfer function being linear across the inside range as shown in FIG. 5 allows achieving a visual effect where the primary region of interest appears, e.g., at higher contrast than the remaining region(s) as shown in FIG. 3B,D. This allows better user interaction as the user can better focus on the primary region but is still provided with some (simplified) structural information about the remaining region(s). The risk of user distraction is lowered whilst the user is still provided with a broad overview of the remaining region(s).

Referring back to FIG. 3, upper row (panes A,B) in FIG. 3 is an illustration of one coronal slice of a typical 3D thorax CT image. In particular, pane A is a visualization of a thorax scan as per standard level-window settings for the lungs (coronal view of thorax CT scan using a HU range of −800 to −100). Hence the lungs can be optimally viewed, but all inner organs with higher HU values "vanish" in homogenous image regions 202, eg, muscles, fat and bone all appear white, everything outside the body (clothing, blanket, . . . ) appears black in this example. In contrast, imagery obtainable by the proposed visualizer VS is shown in pane B. The lung level-window settings are not changed, hence the lungs can be reviewed as before, but additionally the inner body structures 204 are now visible around the lung region clearly standing out against the previously (pane A) homogenous background. Of lesser relevance herein, but still illustrative to show the effectiveness of the proposed system to include contextual information, it is of note, that even other structures, such as folds of a blanket (of the patent) are discernible outside the body region.

Lower row (panes C,D) in FIG. 3 is an illustration of one axial slice of a typical 3D pelvis CT image. In more detail, pane C illustrates a visualization of a pelvis scan as per standard level-window settings for good soft tissue contrast (CT dataset of pelvis using HU range of −100 to +100). With this setting the bone appears white and internal bony structure is hence not visible any more. Pane D is a visualization of the same image as per the proposed visualizer VS. Soft tissue contrast is the same as before, but now the bone structures are better resolved with previously (pane C) hidden transition structures emerging.

In both examples B,D, the respective transfer functions outside the selected window are mapping to gray values, which have already been used in the inside region, e.g. see that the previously black background now appear mostly white. However, in the background the contrast is not so much within structures themselves, but rather at structure transitions. In this way, we achieve that the image appearance for the outside region is different (from the rendering of the inside region), thus indicating to the user the rendering of the outside region is additional to the information as per the rendering of the inside region. Thus a reviewer does not get distracted by strong contrasts or colors in the region which would have been rendered as background.

Of course, the image values in the outside range do not have to be gray values, but may be true colors. For instance, the region of the outside range "above" (or to the right) of the level-window may be rendered in shades of one color and the region "below" (or to the left) of the chosen level-window may be rendered in (other) shades of the same or another color, or rendering may comprise transition through rainbow colors spectrum. Using different colors or shadings for the different parts of the outside range is useful in particular for low contrast/low resolution screens such as handheld devices (smartphones, laptops etc), especially when used in bright environments such as outdoors.

Preferably, tone changes are selected at HU values with locally minimal iso-surface areas as it has been observed that a "true" surface, e.g. skin, has (much) smaller iso-surface area, than, say, an "artificial" surface due to noise, where almost every voxel is a surface voxel. For CT images, these values are related to the transitions of the HU value-ranges between different tissue classes: air, water, fat, bone and metal. In other words, the proposed visualizer VS generates a complementary additional transfer function with contrast at meaningful iso-levels outside the selected window. For the display of MR images, these values should be chosen dynamically, i.e. for every individual image anew, with the techniques described in V Pekar et al, "Fast detection of meaningful isosurfaces for volume data visualization", IEEE VIS '01 Proceedings of the conference on Visualization 2001, pp 223-230.

As can be seen (panes B, D in FIG. 3), the visualizations produced by the proposed visualizer VS is intrinsically capable of making discernable transition structures in the outside region alongside the image information as per the inside region. There is no need for extra graphical auxiliaries such as overlays or some such (although, of course, such graphical overlays can still be used) to highlight these transition structures which can be distracting for the clinician who are juggling a large workload in the ever busy clinical environments of today where time is at a premium. The proposed visualizer strikes a useful middle ground between providing focused structural information on the inside range and at the same time furnishing to the user additional structural information as per the outside range. Because the visualization in the outside range highlights only those transition points that carry enough information (as measured against a metric discussed in more detail below), this middle ground can be achieved without drowning the user in too much detail. The proposed visualizer encourages an out-of the-box mindset where the user can keep an eye on the anatomical context surrounding the primary region of interest.

Very briefly, the proposed visualizer VS generates the second transfer function in addition to the transfer function specified by the user or by a protocol. The second transfer function is configured to emphasize, when used for rendering, certain salient features of structures represented by intensity values in the outside range. More particularly the proposed visualizer VZS analyses information in the outside range to find regions or points of transition and the second transfer function is then configured to effect maximal contrast at those transition points/regions. Of course the proposed visualizer can also be used to generate not just one but two or more additional transfer functions for said outside range of intensity values of the first transfer function.

Referring back to the block diagram in FIG. 1, components of visualizer VS are first briefly introduced before explaining operation in greater detail further below at flow chart FIG. 4.

The visualizer VS includes an input port IN at which the intensity values (as converted from signals acquired by the image acquiring apparatus) are received. The visualizer further receives a specification of a transfer function as specified for instance by a user, which transfer function is thought to be suitably configured for a particular primary region of interest. The definition of the transfer function includes in particular definition of the outside range and the inside range of intensity values as explained above in FIG. 2. A transition region identifier TRI then examines the outside region intensity values and identifies therein one or more transition points. Those points are thought to represent structures of potential interest such as intensity levels that represent transitions in structure, composition or configuration or otherwise. A transfer function generator GFT then generates a second transfer function restricted to the outside intensity values. This transfer function is so configured that it is capable of generating maximum contrast at precisely those identified transition points or at least locally maximum contrast in respective neighborhoods around the transition point(s). This means in particular that the second transfer function so configured has locally maximum slope or at least a very large slope (compared to neighboring slopes) at precisely those transition points. The second transfer function is then used by a renderer RD to generate the visualization in an otherwise known manner and to pass on at an output port (not shown) control signals to the video system VD to effect generation of the visualization on the display unit MT. In one embodiment operation of the transition region identifier TRF is based on examining iso-surfaces in the received image data for the outside region. The iso-surfaces are then evaluated to so identify the transition points or regions. For instance, a suitable metric to assess whether or not there is a transition point includes computing the area size of the iso-surface and/or computing gradients or an integral of gradients across said iso-surfaces. Also the absolute value of the gradient may be considered. The metric is compared against suitably defined thresholds to establish whether there is or is not a transition point. In addition to producing visualization that shows highest contrast at said transition points, the renderer may be configured to include graphic representations of the iso-lines in form of contour lines of those iso-surfaces that yielded a transition point.

Figure 4:
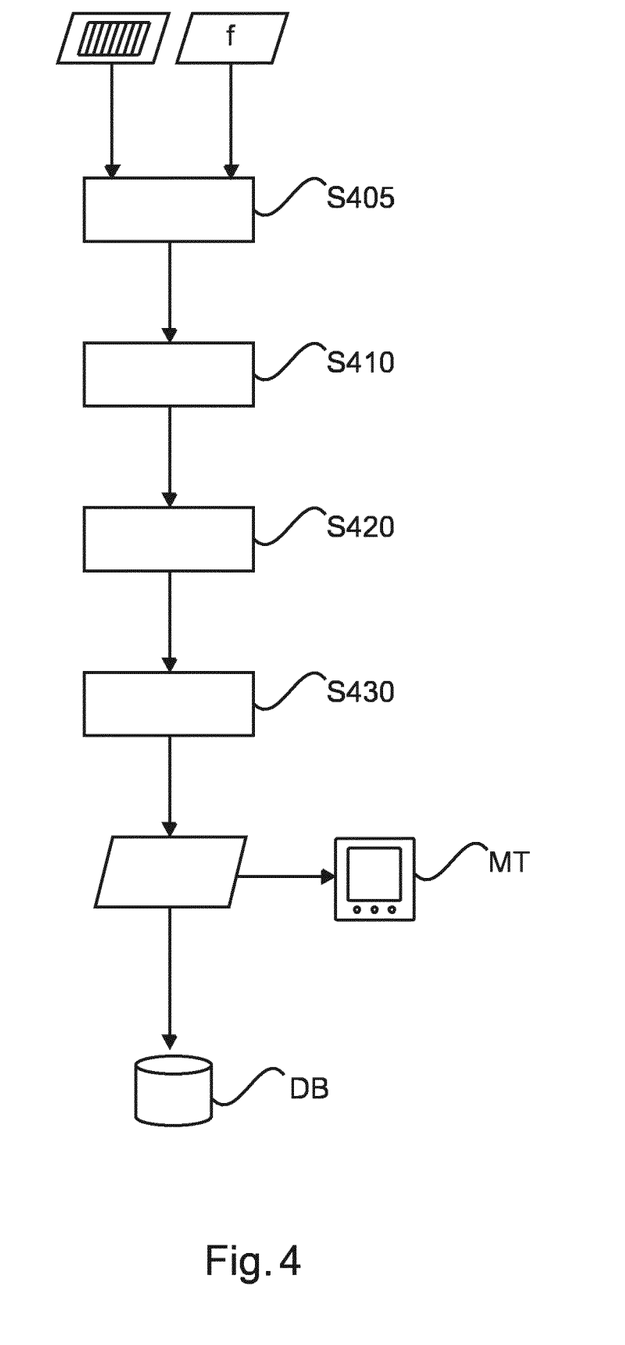
FIG. 4 shows a flow chart of an image processing method.

Referring now to FIG. 4, operation of the proposed visualizer VS is explained in more detail. It will be appreciated however, that the flow chart in FIG. 4 and the description that follows is not necessarily tied to the architecture as laid out in FIG. 1 and the algorithm or image processing method as per flow chart in FIG. 4 can be read in its own right also.

At step S405 the image raw data as defined by a range of intensity values (with or without conversion) is received. Not necessarily concurrently with said intensity values. a specification of proposed first transfer function is received. This first transfer function is configured or "tailored" for a first (primary) region of interest. The first or primary transfer function may be generated by the user manually or may be generated automatically on instruction by a suitable imaging protocol. The first transfer function induces a partition on the range of intensity values into an inside range and an outside range. The outside range is in one embodiment formed by those intensity values that are mapped to constant color values by the first transfer function.

At step S410 the outside range of the intensity values are examined to identify points or regions thereof that are representative of compositional or structural or otherwise transitions in the imaged object. According to one embodiment the method of Pekar et al (referenced above) is used which is based on analyzing iso-surfaces within the intensity values in the outside range. More particularly, the method in Pekar can be used to find iso-values whose iso-surfaces with interesting structures. The iso-levels so found are known to maximize certain criteria as now explained in more detail.

The identifying step at S410 may include in particular an evaluating step to evaluate information as encoded by the iso-surfaces by means of a suitable metric. The evaluation operation seeks to establish local behavior/structure of the iso-surface that is a tell-tale for said transitions. The term "iso-surface" is used herein in the general sense and includes in particular "1-dimensional surfaces" (a line that is) in case the set of intensity values is 2D (as in planar radiography) rather than 3D (as in CT).

Using the method of Pekar, once these iso-levels are computed, for one or more (or each) intensity value (e.g. voxel gray value) in the outside range, the iso-surface (or the sub-volume in a range around this value) is evaluated applying the metric: embodiments envisaged for a suitable metrics includes computing an area of the respective iso-surface. In another embodiment, the metric is implemented as an integral function. More particularly, an image gradient across, that is, perpendicular to the respective iso-surface is integrated to obtain a score under said metric. In other embodiments, the metric involves computing an absolute value of the gradient to assess "gradient strength". Alternatively, gradient behavior may also be assessed in "directed fashion" by looking at the signed gradient rather than its absolute value to learn whether the gradient strength is directed to the inside or outside of the iso-surface.

These metrics indicate a change of the image values along the respective iso-surface. In other words, the score returned by the metric can be thought to quantify a magnitude of the transition one wishes to identify in the set of intensity values. The methodology in Pekar has been found to be computationally (very) cheap so the metric (eg, the integral function) can be computed in reasonable time for each intensity value in the outside range. The local or global extrema (maxima or minima) of this metric function in the outside range can then be recognized to yield loci of transitions, that is, the image content at these loci is relatively rich in additional information.

Although the Pekar paper has been referenced above at a number of occasions it will be understood that this is merely an exemplary embodiment only and other suitable analyzing techniques may be used as well. For instance, in other embodiments the evaluation operation may include computing other functions such as linear maps and examining their eigenvalues which are then compared against suitable chosen thresholds. For instance, the iso-surface may be locally approximated by linear operators (such as the Hessian matrix) and examining the eigenvalues of this matrix allows assessing the nature of the iso-surface which may again provide clues on whether the iso-surface represents a transition.

To summarize the above, and according to some embodiments, the evaluation operation operates on the iso-surfaces. It may evaluate such properties as e.g. the area, the average intensity, the gradient-absolute-value across the iso-surface, a local feature response or others. The result of the evaluation operation could be required to be above or below a threshold to qualify the intensity value generating this iso-surface as a transition value. Another qualification criterion for there to be a transition point is that the metric used for the evaluation operation, as a function of the intensity value (that corresponds to iso-surface) returns at least a local (if not a global) extremum (maximum or minimum). Said differently, the identified intensity values are those where the integral absolute gradient value is at least locally maximal or where the absolute gradient across the iso-surface is above a certain threshold or whose iso-surface area is locally minimal or below a certain threshold.

At step S420 a second transfer function which is different from the first transfer function is generated for the outside set of intensity values. The transfer function is so configured that it assumes its largest slope (gradient that is) at precisely those transition points as identified in the previous step S410. In other words, the second transfer function returns the largest contrast at said transition points/regions in the outside range, that is, outside the pre-defined level-window range of the first transfer function. The largest slope may or may not be a global maximum in other words, a mere locally maximum (in a certain neighborhood around the transition points) may be sufficient. Alternatively, it may not be necessary for the largest slopes to occur exactly at the transition points. It may be sufficient to have at the largest or at locally maximal slope to occur at outside values close to the actual transition points. In particular, the second transfer function is non-linear in the (whole of the) outside range whilst the first transfer function is in general linear in the (whole of the) inside range.

The (locally) maximal slopes envisaged for the transition points (or for points close to the transition points) may be determined automatically or may be prescribed by the user. Once the location of the transition points are known, the second transfer function can be computed as a zig-zag as per FIG. 5 A or by using a Bezier curve module to compute a curve (which is nowhere linear) to pass through the transition points as control points with the prescribed slopes.

At step S430 visualization is generated based on the (at least) two transfer functions. As explained above, panes B,D show exemplary imagery obtainable with the proposed method. Optionally, and in some embodiment, in addition, iso-lines are drawn lines to enhance the contrast as per the second transfer function. The second transfer functions together with the original transfer function or in isolation therefrom may be stored on a suitable memory device MEM such as a data base etc for future reference.

Some or all of the above described steps may be initiated automatically upon receipt of the intensity data at step S405. The user, upon loading the intensity data, is presented with the visualization without user interaction. Other, more interactive embodiments are also envisaged herein. For instance, in one embodiment, an initial visualization based on the first transfer function displayed first, including the one or more homogenous regions 202 equalized by the action of the first transfer functions. The user then specifies by touch screen action or by operation of a pointer tool (computer mouse or stylus, etc) the region 202 for which more structure is sought. In response to this request, the visualization based on the two (or more) transfer functions as per rendering step S430 is then generated. In one embodiment, the processing steps S410, S420 are carried out, in a pre-processing phase, upon receiving the intensity data at step S405 and it is only the rendering step S430 that is then delayed. The rendering step is then carried out only when the user request is received. Alternatively, all steps S410-S430 are carried out only upon receipt of the user request.

In another exemplary embodiment of the present invention, a computer program or a computer program element is provided that is characterized by being adapted to execute the method steps of the method according to one of the preceding embodiments, on an appropriate system.

The computer program element might therefore be stored on a mobile or stationary computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular bot necessarily a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   a data processor; and
   a computer-readable medium storing a computer program executable by the data processor to:
   receive i) image data comprising a range of intensity values converted from signals acquired by an imaging apparatus in respect of an imaged object, and ii) a definition of a first transfer function configured to map an inside range within said range of said intensity values to an image interval of image values wherein the first transfer function is linear with a same non-zero slope for the entire inside range;
   identify from among intensity values of an outside range that is outside of the inside range, one or more transition intensity values representative of a transition in respect of a physical property in relation to said imaged object;
   generate for said outside range of intensity values, at least one second transfer function, said at least one second transfer function being non-linear and having a respective non-zero gradient at or around the one or more transition intensity values, said at least one second transfer function using the intensity values of the outside range of intensity values; and
   render, on a display unit, a visualization of at least a part of said image data, the visualization being generated by operations including mapping intensity values of the image data that are in the inside range using the first transfer function and mapping intensity values of the image data that are in the outside range of intensity values using the at least one second transfer function.

2. The image processing system as per claim 1, wherein a transition region is identified by computing at least one iso-surface for said outside range of intensity values, wherein the identification of said more transition intensity values is based on an evaluation of said at least one iso-surfaces.

3. The image processing system as per claim 2, wherein said evaluation of said at least one iso-surfaces includes computing a metric, said metric being any one or more of the following: a surface area of said at least one iso-surface, a gradient across said iso-surface, and a computed integral of a gradient or of an absolute or signed value of a gradient.

4. The image processing system as per claim 3 wherein the one or more transition intensity values are identified if the metric returns a value above or below a threshold.

5. The image processing system as per claim 2, wherein the visualization is generated by a further operation of including one or more contour-lines of the at least one iso-surfaces in the visualization.

6. The image processing system as per claim 1, wherein the imaged data is any of: a 2D X-ray image, a 3D computed tomography image volume, a magnetic resonance image data, or a 2D or 3D ultrasound image.

7. The image processing system as per claim 1, wherein the transition in relation to said imaged object includes a material type transition or a transition between material type and background.

8. An image processing method, comprising:
   receiving, at a data processor, i) image data comprising a range of intensity values converted from signals acquired by an imaging apparatus in respect of an imaged object, and ii) a definition of a first transfer function configured to map an inside range within said range of said intensity values to an image interval of image values, wherein the first transfer function is linear with a same non-zero slope for the entire inside range;
   using the data processor, identifying from among intensity values outside said inside range, referred to herein as outside intensity values, one or more transition intensity values representative of a transition in respect of a physical property in relation to said imaged object;
   using the data processor, generating for said outside intensity values, at least one second transfer function that uses the outside intensity values, said at least one second transfer function being non-linear and having a respective non-zero gradient at or around the one or more transition intensity values; and
   rendering, on a display unit, a visualization of at least a part of said image data based on the first and second transfer functions;
   wherein the visualization is generated by operations including mapping intensity values of the image data that are in the inside range using the first transfer function and mapping intensity values of the image data that are outside of the inside range using the at least one second transfer function.

9. An image processing system, comprising:
   a data processor; and
   a computer-readable medium storing a computer program executable by the data processor to:
   receive image data comprising a range of intensity values converted from signals acquired by an imaging apparatus in respect of an imaged object;
   generate a visualization of at least a part of said image data by operations including mapping intensity values of the image data that are in an inside range using a first transfer function and mapping intensity values of the image data that are in an outside range of intensity values that is outside of the inside range using a second transfer function; and
   render the visualization on a display unit;
   wherein the first transfer function is linear with a same non-zero slope for the entire inside range, and the second transfer function uses the intensity values of the outside range of intensity values and is non-linear and has a respective non-zero gradient at or around one or more transition intensity values that are outside said inside range wherein the one or more transition intensity values are representative of a transition in respect of a physical property in relation to the imaged object.

10. The image processing system of claim 9 wherein the second transfer function has at least one peak or trough that is aligned with respective peaks in a pixel data value histogram of the image data.

11. The image processing system of claim 9 wherein the second transfer function includes two or more peaks or troughs that are aligned with respective fat and water peaks in a pixel data value histogram of the image data.

12. The image processing system of claim 9 wherein the second transfer function is an oscillating function.

13. The image processing system of claim 9 wherein the imaged data is any of: a 2D X-ray image, a 3D computed tomography image volume, a magnetic resonance image data, or a 2D or 3D ultrasound image.

* * * * *